US012685752B2

(12) United States Patent
You

(10) Patent No.: US 12,685,752 B2
(45) Date of Patent: Jul. 21, 2026

(54) COMPOSITION FOR KIDNEY TREATMENT USING OMENTUM, A MEDICAL KIT FOR KIDNEY TREATMENT, INCLUDING THE SAME, AND FILM FOR KIDNEY TREATMENT, INCLUDING CURED PRODUCT THEREOF

(71) Applicant: ROKIT HEALTHCARE INC., Seoul (KR)

(72) Inventor: Seok Hwan You, Seoul (KR)

(73) Assignee: ROKIT HEALTHCARE INC., Seoul (KR)

( * ) Notice: Subject to any disclaimer, the term of this patent is extended or adjusted under 35 U.S.C. 154(b) by 0 days.

(21) Appl. No.: 17/442,027

(22) PCT Filed: Apr. 9, 2021

(86) PCT No.: PCT/KR2021/004497
§ 371 (c)(1),
(2) Date: Sep. 22, 2021

(87) PCT Pub. No.: WO2021/241880
PCT Pub. Date: Dec. 2, 2021

(65) Prior Publication Data
US 2023/0072749 A1     Mar. 9, 2023

(30) Foreign Application Priority Data

May 29, 2020    (KR) ........................ 10-2020-0065439
Apr. 9, 2021    (KR) ........................ 10-2021-0046267

(51) Int. Cl.
| A61K 35/36 | (2015.01) |
| A61K 9/00 | (2006.01) |
| A61K 38/36 | (2006.01) |
| A61K 38/48 | (2006.01) |
| A61P 13/12 | (2006.01) |

(52) U.S. Cl.
CPC ............ *A61K 35/36* (2013.01); *A61K 9/0024* (2013.01); *A61K 38/363* (2013.01); *A61K 38/4833* (2013.01); *A61P 13/12* (2018.01)

(58) Field of Classification Search
CPC .... A61K 31/36; A61K 9/0024; A61K 38/363; A61K 38/4833; A61K 35/12; A61K 38/39; A61K 9/008; A61P 13/12; A61L 27/16; A61L 27/18; A61L 27/20; A61L 27/225; A61L 27/50; A61L 27/3604; A61L 2400/06; A61L 2430/26
See application file for complete search history.

(56) References Cited

U.S. PATENT DOCUMENTS

| 2015/0202348 A1 | 7/2015 | Dvir et al. |
| 2015/0352145 A1 | 12/2015 | Matheny |
| 2018/0361023 A1* | 12/2018 | Dvir .................... A61L 27/3604 |

FOREIGN PATENT DOCUMENTS

| CN | 101945676 A | 1/2011 |
| KR | 2014-0123516 A | 10/2014 |
| KR | 2019-0098907 A | 8/2019 |
| WO | 2009/085547 A2 | 7/2009 |
| WO | 2019/151611 A1 | 8/2019 |

OTHER PUBLICATIONS

Garcia Gomez (Activated Omentum Slows Progression of CKD), J Am Soc Nephrol 25: 1270-1281, 2014.*
Ignacio Garcia-Gomez et al., "Activated Omentum Slows Progression of CKD", J Am Soc Nephrol, vol. 25, No. 6, p. 1270-1281 (12 pages).
Office Action issued in counterpart Korean Patent Application No. 10-2021-0128587 issued Mar. 29, 2024 (14 pages).
First Office Action issued in counterpart Chinese Patent Application No. 202180002778.4 issued Nov. 14, 2023 (11 pages).

* cited by examiner

*Primary Examiner* — Zohreh A Fay
(74) *Attorney, Agent, or Firm* — Osha Bergman Watanabe & Burton LLP

(57) ABSTRACT

The present invention provides a composition for kidney treatment using the omentum, a medical kit for kidney treatment including the composition for kidney treatment using the omentum, and a film for kidney treatment including a cured product of the composition for kidney treatment using the omentum.

4 Claims, 6 Drawing Sheets

[Fig. 1]
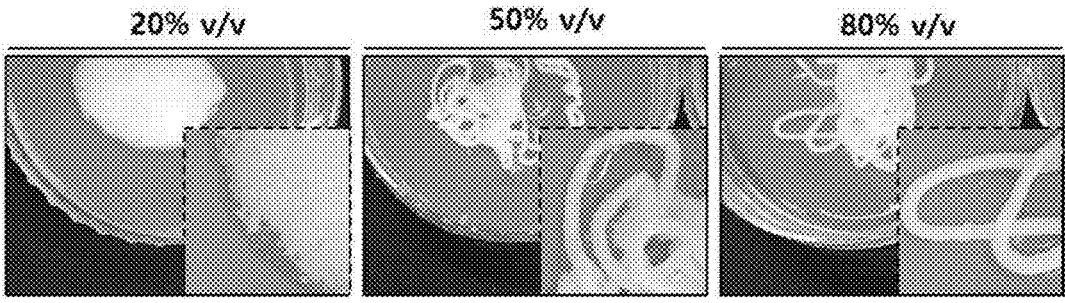
[Fig. 2]
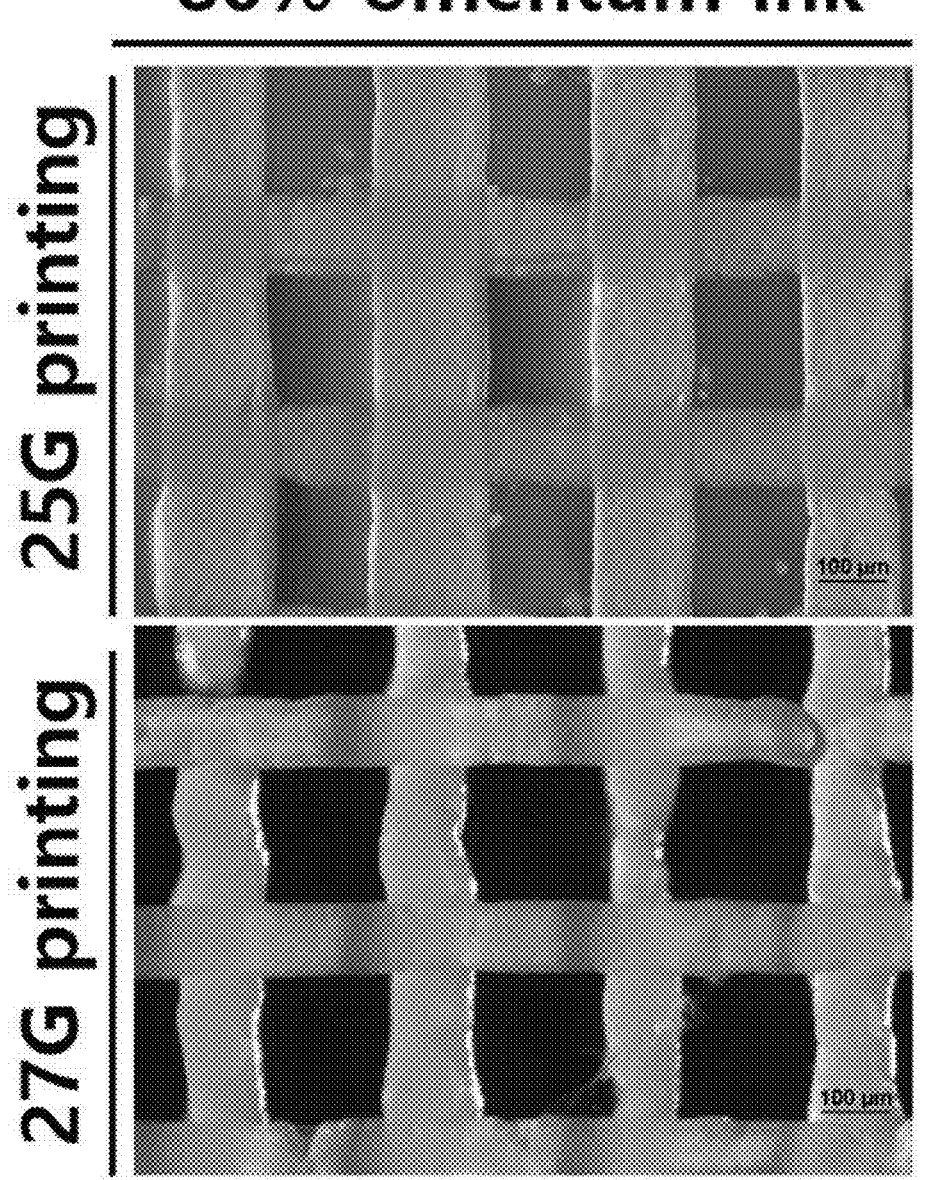

[Fig. 3]
| Omentum | Fibrin glue | Film | Handling |
|---------|-------------|------|----------|
| 20 vol. % | 80 vol. % | | |
| 50 vol. % | 50 vol. % | | |
| 80 vol. % | 20 vol. % | | |
[Fig. 4]
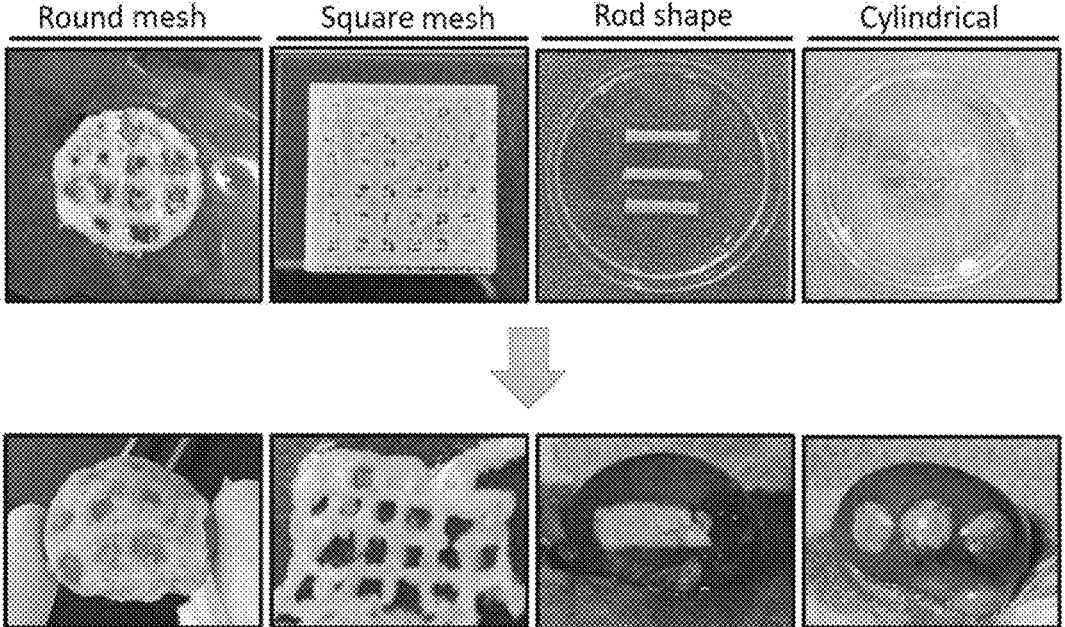

[Fig. 5]
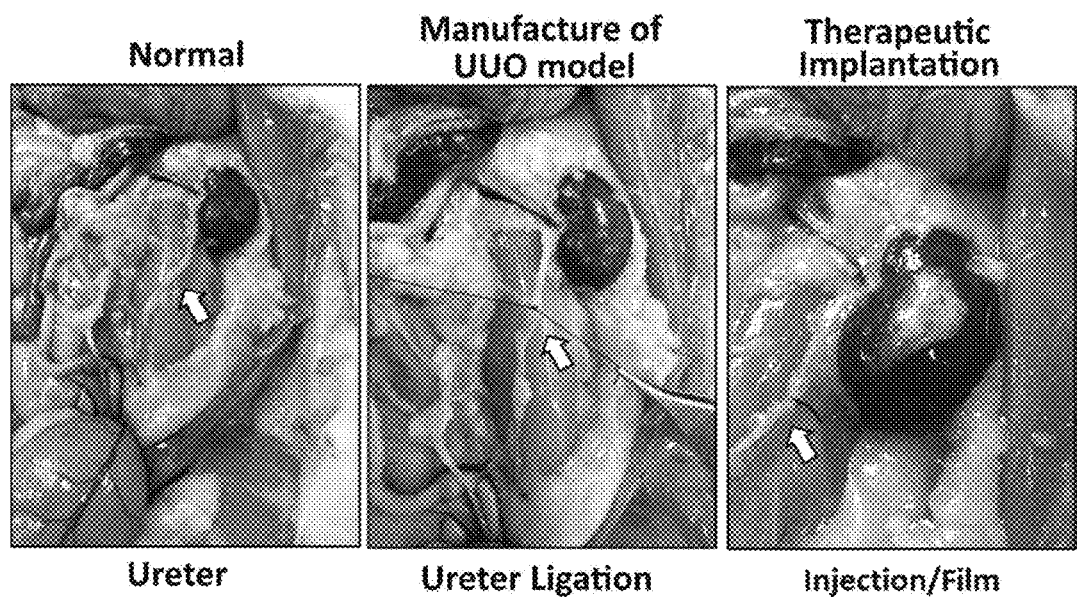
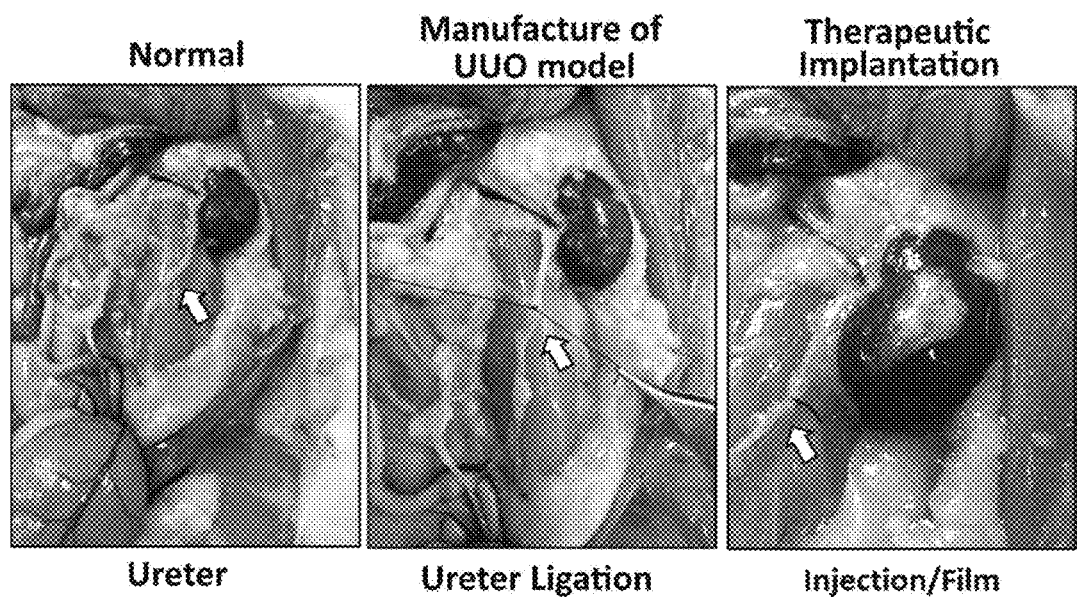
\* White arrow : ureter

[Fig. 6]
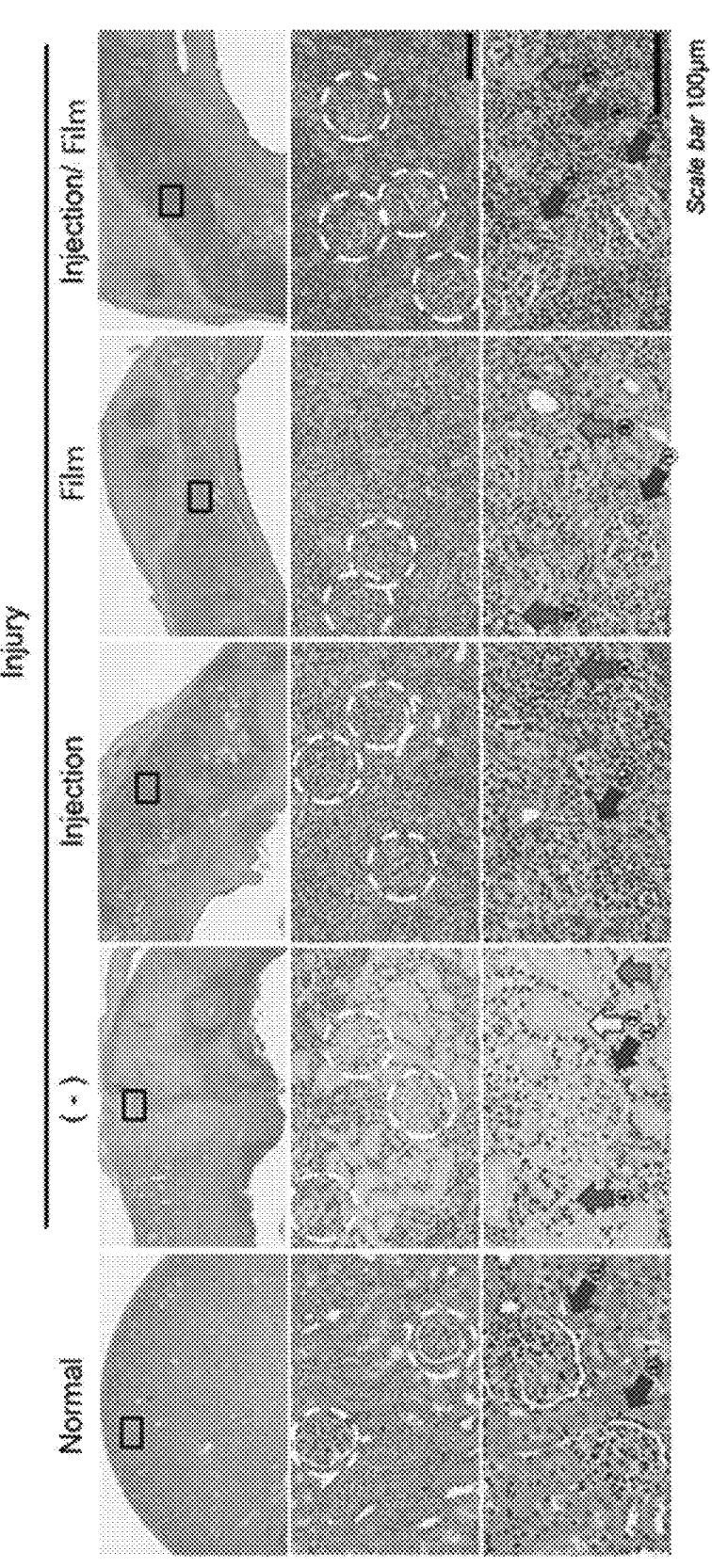

[Fig. 7]
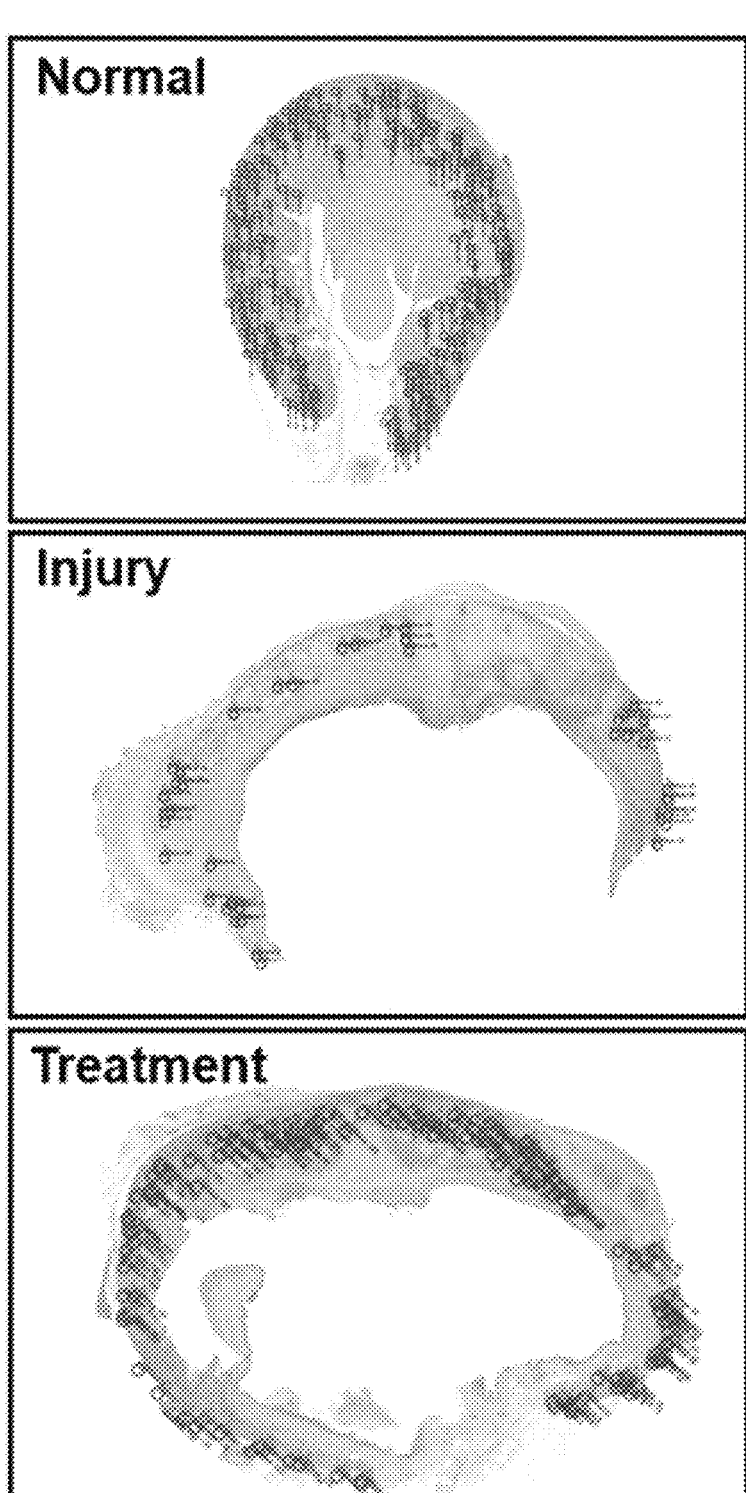
Point : Glomerulus

[Fig. 8]
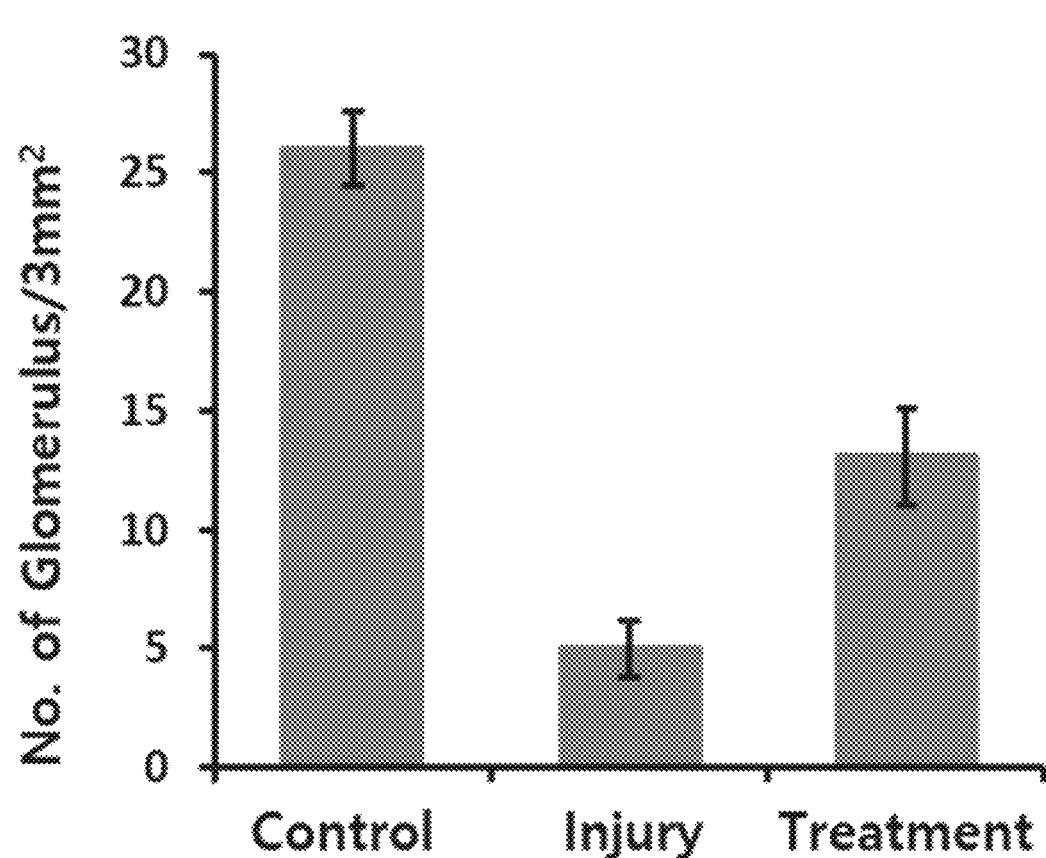

COMPOSITION FOR KIDNEY TREATMENT USING OMENTUM, A MEDICAL KIT FOR KIDNEY TREATMENT, INCLUDING THE SAME, AND FILM FOR KIDNEY TREATMENT, INCLUDING CURED PRODUCT THEREOF

CROSS-REFERENCE TO RELATED APPLICATION

This application claims priority to and the benefit of Korean Patent Application No. 10-2020-0065439, filed on May 29, 2020, the disclosure of which is incorporated herein by reference in its entirety.

TECHNICAL FIELD

The specification relates to a composition for kidney treatment using the omentum, a medical kit for kidney treatment, which includes the composition for kidney treatment using the omentum, and a film for kidney treatment, which includes a cured product of the composition for kidney treatment using the omentum.

BACKGROUND

Although the number of deaths caused by acute complications of diabetes decreased due to the recent advancement of medicine, macrovascular and microvascular complications, belonging to chronic complications caused by diabetes, are increasing. Particularly, a diabetic kidney disease, which is one of the microvascular complications of glomeruli, is a disease which is the most important cause of end stage renal disease (ESRD), and accounts for the highest frequency of mortality due to diabetic complications.

As common pathological findings of the diabetic kidney disease, there are the thickening of glomeruli and renal tubules due to hyperglycemia, the proliferation of mesangial cells, and the accumulation of the mesangial matrix. Continuous progression of these phenomena leads to glomerulosclerosis, eventually causing renal dysfunction such as renal failure.

Since symptoms of a kidney disease slowly appear, it is difficult to recognize a chronic kidney disease and thus treatment time is often missed. To prevent a chronic kidney disease, it is necessary to undergo periodic checkups, and when the disease has developed to a chronic kidney disease, there are currently no apparent therapeutic methods other than dialysis or transplantation.

PATENT DOCUMENT

Korean Unexamined Patent Application Publication No. 10-2014-0123516

SUMMARY

The present invention is directed to providing a composition for kidney treatment using the omentum, a medical kit for kidney treatment, which includes the composition for kidney treatment using the omentum, and a film for kidney treatment, which includes a cured product of the composition for kidney treatment using the omentum, which can help the recovery of kidneys of a patient with a kidney disease. Specifically, the present invention is directed to providing a composition for kidney treatment for recovering the damaged kidney of a kidney disease patient in which a glomerular filtration rate is decreased to 60/ml/min/1.73 m$^2$ or less or a kidney disease patient diagnosed to have an albuminuria of 30 mg/gCr or more.

One aspect of the present invention provides a composition for kidney treatment using the omentum, which includes a micronized omentum tissue extract; and a bioadhesive.

Another aspect of the present invention provides a medical kit for kidney treatment, in which the composition for kidney treatment using the omentum is charged into a syringe for human injection.

Still another aspect of the present invention provides a film for kidney treatment, which includes a cured product of the composition for kidney treatment using the omentum.

Advantageous Effects

A composition for kidney treatment and/or film for kidney treatment using the omentum according to the present invention has advantages of preventing renal dysfunction or recovering a renal function through a minimal procedure.

In addition, since it uses autologous tissue, the composition for kidney treatment and/or film for kidney treatment using the omentum according to the present invention can provide an environment suitable for cell survival when applied to the human body, and the materials released therefrom have an advantage of increasing the cell activity of damaged tissue by delaying renal fibrosis, which is the pathological characteristic of chronic renal failure, and inhibiting the necrosis of renal cells.

BRIEF DESCRIPTION OF THE DRAWINGS

FIG. 1 shows the results of discharging a composition for renal treatment using a 3D bioprinter according to Experimental Example 1.

FIG. 2 shows the results of manufacturing a film for renal treatment using a 3D bioprinter according to Experimental Example 1.

FIG. 3 shows the results of manufacturing a rod-type film for renal treatment according to Experimental Example 1.

FIG. 4 shows various shapes of a film for renal treatment manufactured according to Example 1 and examples to which the film is applied.

FIG. 5 illustrates the manufacture of an UUO model according to Experimental Example 2 and the UUO model to which the composition for renal treatment is applied.

FIG. 6 shows the staining results for renal tissue according to Experimental Example 2.

FIGS. 7 and 8 show the result of quantifying the number of glomeruli in the results according to Experimental Example 2.

DETAILED DESCRIPTION

In the specification, when one component "includes" another component, this means that, unless specifically stated otherwise, other components may be further included, rather than excluded.

In the present invention, when one member is disposed "on" another member, the first member is in contact with the second member, or a third member is interposed between these two members.

Hereinafter, the present invention will be described in detail.

In one embodiment of the present invention, a composition for kidney treatment using the omentum, which includes a micronized omentum tissue extract; and a bioadhesive, is provided.

According to one embodiment of the present invention, the micronized omentum tissue extract may be obtained by grinding extracted omentum tissue.

According to one embodiment of the present invention, the micronized omentum tissue extract may include omentum-derived stromal cells, or an omentum-derived extracellular matrix.

According to one embodiment of the present invention, the omentum-derived stromal cells may be extracted from the omentum, and include mesothelial cells, mesenchymal stem cells (MSCs) and immune cells. The omentum-derived stromal cells may promote the differentiation of renal cells in damaged renal tissue to allow the damaged renal cells to differentiate into renal cells capable of replacing the damaged renal cells.

According to one embodiment of the present invention, the omentum-derived extracellular matrix may be extracted from the omentum, and may be decellularized. The omentum-derived extracellular matrix may release various materials capable of improving the cell activity of the damaged renal tissue, and therefore, the recovery of the damaged renal tissue and additional damage to a kidney may be prevented. Specifically, the omentum-derived extracellular matrix may have a biochemical factor required for the growth and differentiation of renal cells, and provide a physical environment in which the omentum-derived stromal cells can be fixed after differentiating into renal cells.

According to one embodiment of the present invention, the micronized omentum-derived tissue extract may be derived from autologous or allogeneic omentum.

According to one embodiment of the present invention, the micronized omentum-derived tissue extract may be derived from the great omentum.

According to one embodiment of the present invention, the micronized omentum-derived tissue extract may be derived from autologous or allogeneic omentum. The omentum-derived tissue is preferably derived from autologous omentum. Specifically, according to one embodiment of the present invention, the micronized omentum-derived tissue extract may be derived from autologous great omentum.

According to one embodiment of the present invention, the micronized omentum-derived tissue extract may include omentum-derived tissue particles having an average particle diameter of 5 μm or more and 200 μm or less. The average particle diameter of the omentum-derived tissue particles may be measured using laser quenching using a particle analyzer, or using a scanning electron microscope. In addition, it may also be determined whether the pore diameter corresponds to the average particle diameter by whether the particles pass through a filter having a pore diameter of 5 μm or more and 200 μm or less.

According to one embodiment of the present invention, the micronized omentum-derived tissue extract may be obtained by grinding and filtering the extracted omentum or omentum tissue using a series of filters. Specifically, the micronized omentum-derived tissue extract may be obtained by obtaining a first filtrate by mixing the extracted omentum or omentum tissue with normal saline, and grinding and filtering the mixture through a first filter having a pore diameter of 1 to 3 mm; obtaining a second filtrate by grinding and filtering the first filtrate with a second filter having a pore diameter of 400 to 800 μm; and obtaining a third filtrate by grinding and filtering the second filtrate with a third filter having a pore diameter of 5 to 200 μm. The micronized omentum-derived tissue extract may include the third filtrate. Specifically, the micronized omentum-derived tissue extract may include a lower layer precipitated after centrifugation of the third filtrate.

According to one embodiment of the present invention, the step of obtaining a first filtrate may be to obtain a first filtrate by mixing the extracted omentum or omentum tissue with normal saline, grinding and filtering the mixture with a first filter having a pore diameter of 2 to 3 mm, and grinding and filtering the resulting filtrate with an additional first filter having a pore diameter of 1 to 1.5 mm.

According to one embodiment of the present invention, the filter may be a stainless syringe filter, and the grinding and filtration may be performed by equipping syringes at both ends of the filter, and grinding and filtering the target material through the filter one to 30 times, and specifically, 10 to 15 times, using the piston movement of the syringe.

According to the grinding, the omentum or omentum tissue may be grinded into microparticles, and the microparticles may be used as they are, or used by extracting necessary cells. However, a method of grinding the omentum or omentum tissue is not limited, and various methods known in the art may be used.

According to one embodiment of the present invention, the content of the micronized omentum-derived tissue extract may be 40 vol % or more and 90 vol % or less, and specifically, 50 vol % or more and 80 vol % or less. When the content of the micronized omentum-derived tissue extract is less than 40 vol %, due to a high content of the bioadhesive, the composition is easily maintained in a film-like solid shape, but renal cells may not be effectively regenerated due to low activity for kidney treatment. Further, when the content of the micronized omentum-derived tissue extract is more than 90 vol %, it may be difficult to maintain a solid shape, making it difficult to apply the composition to a damaged kidney.

According to one embodiment of the present invention, the bioadhesive may include at least one selected from the group consisting of fibrin glue, collagen, gelatin, a cyanoacrylate-based polymer, a polyurethane-based polymer, a polyglycolic acid-based polymer, a hydrogel, hyaluronic acid, alginate, pluronic F-127, and a cellulose-based polymer. Specifically, the bioadhesive may be fibrin glue and/or gelatin, and more specifically, fibrin glue.

According to one embodiment of the present invention, when the bioadhesive is fibrin glue, the composition for kidney treatment using the omentum may be a two-component composition consisting of a first liquid containing fibrinogen and a second liquid containing thrombin. In addition, the composition for kidney treatment using the omentum may be a two-component composition consisting of a first liquid containing the micronized omentum tissue extract and thrombin, and a second liquid containing fibrinogen. According to one embodiment of the present invention, since the bioadhesive may use fibrin glue consisting of fibrinogen and thrombin, and ensure a higher viscosity than a hyaluronic acid adhesive or collagen adhesive, the film for kidney treatment has excellent adhesion with a diseased site, and further maintains a high strength.

According to one embodiment of the present invention, the composition for kidney treatment using the omentum is a two component-type composition, and the first liquid and the second liquid may be sequentially applied on a damaged renal tissue and reacted, thereby forming a film for kidney treatment on renal tissue in the human body.

According to one embodiment of the present invention, a fibrin matrix through the reaction of fibrinogen and thrombin in the first and second liquids may serve to fix the omentum-derived tissue.

According to one embodiment of the present invention, the concentration of fibrinogen in the first or second liquid may be 4 to 90 mg/mL. In addition, according to one embodiment of the present invention, the concentration of thrombin in the first or second liquid may be 50 to 500 IU/mL.

When the fibrinogen and thrombin concentrations are within the above ranges, it is possible to properly secure a curing rate, and evenly maintain the distribution of the micronized omentum tissue extract in the fibrin matrix. Therefore, by evenly maintaining cell distribution in the film for kidney treatment or patch-type film for kidney treatment, which is formed by injection into the damaged renal cells, cell differentiation capacity in the damaged renal tissue may be effectively achieved. In addition, when the fibrinogen and thrombin concentrations are within the above ranges, the film may be well maintained in a film shape and maintain a suitable hardness, and thus can be properly applied to the diseased site.

According to one embodiment of the present invention, when the first liquid includes fibrinogen, the first liquid may further include aprotinin. The aprotinin is an inhibitor of a proteolytic enzyme secreted from the pancreas, and a polypeptide consisting of a total of 58 amino acids. The aprotinin is mainly extracted from the lung of cattle, and is known to have a hemostatic effect by inhibiting the breakdown of fibrin in blood.

According to one embodiment of the present invention, the aprotinin may be included at 900 to 1,100 Kininogen Inactivator Unit (KIU), and specifically, 1000 KIU, per 1 mL of the first liquid.

According to one embodiment of the present invention, when the second liquid includes thrombin, the second liquid may be prepared by dispersing thrombin in a calcium chloride solution. Specifically, the second liquid may include 40 to 250 IU of thrombin and 5 to 6.5 mg of calcium chloride per 1 mL.

According to one embodiment of the present invention, the composition for kidney treatment using the omentum may further include water as a solvent. Specifically, the composition for kidney treatment using the omentum may further include normal saline. The solvent may include some of a solvent used in grinding of the omentum to obtain the micronized omentum tissue extract, and also include a solvent of the bioadhesive.

According to one embodiment of the present invention, the solvent for the first and second liquids may be water, and specifically, normal saline. In addition, the fibrinogen in the first liquid and the thrombin in the second liquid may be obtained using a commercial fibrin glue kit.

According to one embodiment of the present invention, the composition for kidney treatment using the omentum may be injected into the kidney, specifically, the renal capsule while not solidified, and formed in a film shape in the renal capsule due to curing of a bioadhesive. In addition, the composition for kidney treatment using the omentum may be solidified in a film shape, and applied to the kidney by insertion under the kidney, specifically, the renal capsule.

Specifically, according to one embodiment of the present invention, the composition for kidney treatment using the omentum is a two component-type composition, and may form a film for kidney treatment in the kidney by inducing the reaction of the first liquid and the second liquid by sequentially injecting the first liquid and the second liquid into the kidney. Specifically, a fibrin network may be formed by reacting the thrombin in the second liquid and the fibrinogen in the first liquid, and serves to sufficiently fix the micronized omentum tissue extract.

Since the reaction between the first liquid and the second liquid is completed within five minutes, the first liquid and the second liquid may be sequentially applied on the damaged renal tissue, and specifically, under the renal capsule, using a syringe for human injection, to rapidly facilitate curing. In addition, the composition for kidney treatment using the omentum may be used to immediately form a film for kidney treatment suitable for damaged renal tissue using a 3D printer at the treatment site, which is capable of being implanting into the kidney.

According to one embodiment of the present invention, the composition for kidney treatment using the omentum may have suitable physical properties for passing through 25 G to 30 G injection needles. Specifically, the composition for kidney treatment using the omentum has a viscosity and particles suitable for passing through a 25 G to 30 G injection needle, allowing more precise injection or control of a shape in the formation of the film for kidney treatment. More specifically, the composition for kidney treatment using the omentum may pass through a 30 G fine injection needle, so it can be more precisely injected when injected into the kidney.

According to another embodiment of the present invention, a medical kit for kidney treatment in which the composition for kidney treatment using the omentum is charged in a syringe for human injection is provided. As described above, the composition for kidney treatment using the omentum is injected into the kidney using a syringe for human injection while not being solidified, and then cured to form a film on damaged renal tissue, so it can help the regeneration of the damaged renal cells.

According to one embodiment of the present invention, the medical kit for kidney treatment may include a first syringe for human injection in which the first liquid is charged, and a second syringe for human injection in which the second liquid is charged. As described above, the first liquid is injected and applied on damaged renal tissue using the first syringe for human injection, and the second liquid is applied on the first liquid using the second syringe for human injection, thereby forming a film for kidney treatment on the damaged renal tissue. That is, when the medical kit for kidney treatment is used, there is an advantage in that the procedure for a patient can be performed with minimal invasiveness.

According to another embodiment of the present invention, the film for kidney treatment, which includes a cured product of the composition for kidney treatment using the omentum, is provided.

According to one embodiment of the present invention, the film for kidney treatment may be formed in a rod, mesh or cylindrical shape. The film for kidney treatment may be formed in suitable size and shape according to the shape of the damaged renal tissue and implanted.

According to one embodiment of the present invention, the film for kidney treatment may be formed by curing the composition for kidney treatment using the omentum. In addition, the film for kidney treatment may be formed by applying the composition for kidney treatment using the omentum onto a biodegradable polymer substrate and curing it. The biodegradable polymer substrate may be a porous patch or a scaffold.

According to one embodiment of the present invention, the patch-type film for kidney treatment may allow the induction of a reaction by applying the second liquid on a layer formed by applying the first liquid, and may be formed using a bioprinter known in the art. Specifically, using a Dr. INVIVO-series bioprinter produced by ROKIT Healthcare, a film for kidney treatment may be formed in a form suitable for a diseased site.

According to one embodiment of the present invention, the patch-type film for kidney treatment may have a thickness of 100 µm or more and 1,000 µm or less.

According to one embodiment of the present invention, the film for kidney treatment may have a stiffness of 0.5 kPa or more and 12 kPa or less. The film for kidney treatment may be adjusted to satisfy the stiffness range by adjusting the content of a bioadhesive applied to the composition for kidney treatment. The film for kidney treatment is adjusted within the stiffness range, thereby facilitating handling for insertion into the renal tissue. In addition, the maintenance of a suitable stiffness in the renal tissue affects cell growth, differentiation and migration through a signaling system between cells and the surrounding extracellular matrix to help the recovery of damaged renal tissue.

EXAMPLES

Hereinafter, the present invention will be described in detail with reference to examples to help in understanding the present invention. However, the examples according to the present invention may be modified into a variety of different forms, and it should not be construed that the scope of the present invention is not limited to the following examples. The examples of the present invention are provided to more completely explain the present invention to those of ordinary skill in the art.

Preparation Example (1) Obtaining of Micronized Omentum Tissue Extract

After anesthetizing an experimental mouse, the omentum (specifically, the great omentum) of the experimental mouse was extracted. A syringe containing the great omentum and a new syringe were installed in a two-way inlet of a connector with a stainless syringe filter having a pore diameter of 2.4 mm, and first grinding of the great omentum was performed by passing the great omentum through the stainless syringe filter 11 times by piston movement, and passing it through a stainless syringe filter having a pore diameter of 1.2 mm 11 times by piston movement. Subsequently, second grinding was performed by installing a syringe containing the first grinded filtrate and a new syringe in a two-way inlet of a connector with a stainless syringe filter having a pore diameter of 600 µm, allowing the first filtrate to pass 11 times by piston movement. Finally, third grinding was performed by installing a syringe containing a second grinded filtrate and a new syringe in a two-way inlet of a connector with a stainless syringe filter having a pore diameter of 200 µm and allowing the second filtrate to pass 11 times by piston movement. Therefore, a mixture containing omentum-derived tissue particles having a size of 200 µm or less was washed with an equal amount of normal saline, thereby obtaining a micronized omentum tissue extract.

(2) Preparation of Composition for Kidney Treatment Using Omentum

A first liquid was prepared with 1 mL of an aprotinin liquid in which the obtained micronized omentum tissue extract and 90 mg/mL of fibrinogen were mixed in a volume ratio of 4:1 using a mixing syringe. Here, the final concentration of the fibrinogen in the first liquid was 18 mg/mL.

Further, a second liquid of a calcium chloride solution in which thrombin was dispersed in the same volume as the first liquid was prepared. Here, the concentration of thrombin in the second liquid was approximately 500 IU/mL.

Experimental Example 1

Preparation of Film for Kidney Treatment

Before the formation of a film for kidney treatment using the composition for kidney treatment using the omentum, a viscosity according to a concentration of the composition for kidney treatment using the omentum suitable for a bio 3D printer was confirmed.

A content of a micronized omentum tissue extract in the first liquid of the preparation Example was adjusted to 20 vol %, 50 vol % or 80 vol %, and the micronized omentum tissue extract was discharged using a 3D bioprinter (Dr. INVIVO) produced by ROKIT Healthcare. The results thereof were confirmed.

FIG. 1 shows the results of discharging a composition for renal treatment using a 3D bioprinter according to Experimental Example 1. Specifically, in FIG. 1, when the content of the micronized omentum tissue extract was 20 vol %, due to an excessively low viscosity, it was confirmed that the discharged product does not have a proper shape, and was dispersed. When the content of the micronized omentum tissue extract was 50 vol % or more, it was confirmed that the composition has a viscosity suitable for forming a film in a desired shape such as a mesh type.

FIG. 2 shows the results of manufacturing a film for renal treatment using a 3D bioprinter according to Experimental Example 1. Specifically, in FIG. 2, using a 25 G or 27 G nozzle, a first liquid containing 80 vol % of the micronized omentum tissue extract was discharged in a mesh shape, and then a second liquid was applied and then cured. According to FIG. 2, when the first liquid containing 80 vol % of the micronized omentum tissue extract is used, it was confirmed that a mesh-type film with a preferable shape can be formed.

In addition, after the obtained micronized omentum tissue extract was mixed with fibrin glue, discharged into a rod-shaped mold, and then cured, its handling capacity and shape maintenance were confirmed.

FIG. 3 shows the results of manufacturing a rod-type film for renal treatment according to Experimental Example 1. Specifically, according to FIG. 3, it was seen that as the fibrin glue content is higher, it is preferable for handling capacity and film shape maintenance. However, when the content of the micronized omentum tissue extract that can help the regeneration of kidney cells is low, a kidney treatment effect may be reduced. Therefore, even when the micronized omentum tissue extract is included at a content of 50 vol % or more, since minimal handling capacity and shape maintenance are possible, it was determined that a composition containing 50 vol % or more of the micronized omentum tissue extract is preferable.

FIG. 4 shows various shapes of a film for renal treatment manufactured according to Example 1 and examples to which the film is applied. As confirmed from FIG. 4, the film for kidney treatment according to Example 1 may be formed in various shapes, and suitably applied to a damaged site of the kidney as needed.

Experimental Example 2

Confirmation of Kidney Treatment Effect Using Composition for Kidney Treatment Using Omentum One ureter of an experimental rat was closed so a unilateral ureteral obstruction (UUO) model could be made, which exhibits a histological change such as chronic kidney disease. In this experimental example, the following three types of experiments were performed, and the results were observed.
(Case 1) Injection of Composition for Kidney Treatment Using Syringe The prepared composition for kidney treatment was injected renal subcapsular layer using a syringe, and the effect of kidney treatment was confirmed. Here, the first liquid in the preparation example was injected under the capsule of a damaged kidney area, and then a second liquid was applied to be solidified on the film renal subcapsular layer.
(Case 2) Insertion of Formed Film for Kidney Treatment To discharge the prepared composition for kidney treatment, first, using the hot-melting function of a 3D bioprinter (ROKIT Healthcare, Dr. INVIVO), a frame formed of a polymer material, PCL, was printed in a rod shape with a size of 30 mm×5 mm×0.8 mm (width×length×height). In addition, using a dispenser of the 3D bioprinter, the first liquid was applied to the PCL frame, and then cured using the second liquid, thereby forming a film for kidney treatment. The formed film for kidney treatment was inserted under the capsule of the damaged kidney area.
(Case 3) Insertion of Formed Film for Kidney Treatment and Injection of Composition for Kidney Treatment Using Syringe Using a 3D bioprinter (ROKIT Healthcare, Dr. INVIVO), a composition for kidney treatment prepared in the same manner as the method of forming a film in Case 2 was cured with a second liquid after applying a first liquid in a size suitable for a disease site, thereby forming a film for kidney treatment. The formed film for kidney treatment was inserted subcapsular layer of the damaged renal area. Subsequently, the first liquid in the preparation example was injected into the cortical area under the capsule into which the film for kidney treatment was inserted, and then the second liquid was applied and cured.

FIG. 5 illustrates the manufacture of an UUO model according to Experimental Example 2 and the UUO model to which the composition for renal treatment is applied. Specifically, the arrow in FIG. 5 indicates a ureter, and an UUO model was manufactured by ligating the ureter. It shows that the film for kidney treatment and the composition for kidney treatment are injected into a renal area in which sclerosis occurs were introduced according to Case 3.

FIG. 6 shows the staining results for renal tissue according to Experimental Example 2. Specifically, FIG. 6 shows the results of fixing each of kidney (Normal) in which a UUO model was not applied, injured kidney (−) which is not treated after the UUO model was applied, treatment kidney (Injection) which was treated as in Case 1, treatment kidney (Film) which was treated as in Case 2, and treatment kidney (Injection/Film) which was treated as in Case 3 with a 4% paraformaldehyde solution to form a paraffin block, and then sectioning the paraffin block to a thickness of approximately 4 μm and staining by hematoxylin-eosin (H&E) staining.

In FIG. 6, the dotted circle indicates a glomerular area. In addition, the first arrow indicates a glomerular area, the second arrow indicates a tubule necrosis area, the third arrow indicates an interstitial fibrosis area, and the fourth arrow indicates an immune cell infiltration area.

Specifically, according to the results of FIG. 6, compared to the case in which there was no treatment after applying the UUO model, it was confirmed that in all of Cases 1 to 3 according to Experimental Example, the structure of the glomerulus and cells in the glomerulus maintained a normal shape. Particularly, in the case in which there was no treatment after applying the UUO model, it was confirmed that tubular necrosis (second arrow) occurs, and it was confirmed that, in Cases according to Preparation Example 2, almost no tubular necrosis was found. Therefore, when the composition for kidney treatment using the omentum according to the present invention was applied, it was confirmed that the necrosis/death of nephrons such as glomeruli or tubules was delayed in a kidney injury model, and the damaged cells also recovered.

FIGS. 7 and 8 show the results of quantifying the number of glomeruli in the results according to Experimental Example 2. FIG. 7 shows the number of glomeruli and cell nuclei after renal tissue (Normal) in which an UUO model was not applied, renal tissue (Injury) which was not treated after applying the UUO model, and renal tissue (Treatment) treated as described in Case 1 were stained as described above. Specifically, FIG. 7 shows the glomerulus with points show cell nucleuses. Furthermore, FIG. 8 is a graph obtained by quantifying the results of FIG. 7.

Referring to FIGS. 7 and 8, as a result of calculating the number of glomeruli at eight areas of 3 mm², in the normal tissue (Normal), approximately 26 glomeruli were detected per 3 mm², in the renal tissue (Injury) which was not treated separately after the UUO model was applied, approximately 5 glomeruli were detected per 3 mm². In contrast, in the renal tissue (Treatment) which was treated according to Experimental Example 2, approximately 13 glomeruli were detected per 3 mm². Through these results, it was confirmed that, when the composition for kidney treatment using the omentum according to the present invention was applied, glomerular necrosis was prevented or damage to renal cells was prevented in the UUO model.

The invention claimed is:

1. A method for manufacturing of film for kidney treatment using omentum, comprising:
   forming a mixture of an extracted omentum or an omentum tissue with normal saline;
   grinding and filtering the mixture through a first filter having a pore diameter of 1 to 3 mm to obtain a first filtrate;
   grinding and filtering the first filtrate with a second filter having a pore diameter of 400 to 800 μm to obtain a second filtrate;
   grinding and filtering the second filtrate with a third filter having a pore diameter of 5 to 200 μm to obtain a third filtrate;
   obtaining a micronized omentum-derived tissue extract from the third filtrate;
   preparing a first liquid containing the micronized omentum-derived tissue extract and fibrinogen;
   preparing a second liquid containing thrombin;
   applying the first liquid to form a first layer; and
   applying the second liquid onto the first layer to form a film for kidney treatment by crosslinking the fibrinogen and the thrombin;
   wherein the micronized omentum-derived tissue extract comprises omentum-derived tissue particles having an average particle diameter of 5 μm to 200 μm, wherein the micronized omentum-derived tissue extract comprises omentum-derived stromal cells, and an omentum-derived extracellular matrix, and wherein the content of the micronized omentum-derived tissue extract in the first liquid is 40 vol % to 90 vol %.

2. The method of claim 1, wherein the micronized omentum-derived tissue extract is derived from autologous or allogeneic omentum.

3. The method of claim 1, wherein the micronized omentum-derived tissue extract is derived from great omentum.

4. The method of claim 1, wherein the omentum-derived tissue particles have an average particle diameter of 10 μm to 95 μm.

* * * * *